United States Patent
Henseler et al.

(10) Patent No.: US 9,513,387 B2
(45) Date of Patent: Dec. 6, 2016

(54) SYSTEM AND METHOD FOR PROVIDING DEPTH OF INTERACTION DETECTION USING POSITRON EMISSION TOMOGRAPHY

(75) Inventors: Debora Henseler, Erlangen (DE); Matthias J. Schmand, Lenoir, TN (US); Ronald Grazioso, Knoxville, TN (US)

(73) Assignees: Siemens Aktiengesellschaft, Munich (DE); Siemens Medical Solutions USA, Inc., Malvern, PA (US)

( * ) Notice: Subject to any disclaimer, the term of this patent is extended or adjusted under 35 U.S.C. 154(b) by 1406 days.

(21) Appl. No.: 13/017,617

(22) Filed: Jan. 31, 2011

(65) Prior Publication Data

US 2011/0192982 A1    Aug. 11, 2011

Related U.S. Application Data

(60) Provisional application No. 61/300,146, filed on Feb. 1, 2010.

(51) Int. Cl.
| | |
|---|---|
| *G01T 1/20* | (2006.01) |
| *G01T 1/29* | (2006.01) |
| *G01T 1/164* | (2006.01) |
| *A61B 6/03* | (2006.01) |

(52) U.S. Cl.
CPC ........... *G01T 1/2985* (2013.01); *G01T 1/2008* (2013.01); *A61B 6/037* (2013.01); *G01T 1/1644* (2013.01); *G01T 1/2002* (2013.01)

(58) Field of Classification Search
CPC .............................. G01T 1/2002; G01T 1/1644
USPC .............................................. 250/368, 361 R
See application file for complete search history.

(56) References Cited

U.S. PATENT DOCUMENTS

| | | | |
|---|---|---|---|
| 6,288,399 B1 | 9/2001 | Andreaco et al. | |
| 7,019,297 B2 | 3/2006 | Aykac et al. | |
| 2004/0178347 A1* | 9/2004 | Murayama et al. | 250/367 |
| 2004/0262526 A1* | 12/2004 | Corbeil et al. | 250/367 |

(Continued)

OTHER PUBLICATIONS

"Improvement of the Depth of Interaction Detector for PET on Full Energy Pulse Height Uniformity," IEEE Transactions on Nuclear Science, vol. 50, No. 5, Oct. 2003, p. 1439-1443 to Kasahara et al.*

(Continued)

*Primary Examiner* — David J Makiya
*Assistant Examiner* — Kenneth J Malkowski

(57) ABSTRACT

A system and method is provided for determining depth of interaction (DOI) information. The system and method includes a detector configured to generate DOI information as a result of radiation emitted from a radiation source. The system and method further includes a plurality of scintillator pixels forming a block, wherein the plurality of scintillator pixels have a first portion and a second portion. A first medium distributed in an alternating pattern of coupling and separation between each of the scintillator pixels in a first portion or second portion of the block is also provided. A plurality of sensors for detecting scintillation events across the plurality of scintillators based on the alternating pattern of coupling and separation between each of the scintillator pixels, wherein DOI information is provided by a position profile of the block, and an image processor for generating a 3 dimensional image from the DOI information are also included.

15 Claims, 9 Drawing Sheets

(56) References Cited

U.S. PATENT DOCUMENTS

2007/0090298 A1    4/2007  Shao

OTHER PUBLICATIONS

Cayouette, et al., "Monte Carlo simulation using DETECT2000 of a multilayered scintillation block and fit to experimental data," Nuclear Science, IEEE Transactions on , vol. 50, No. 3, pp. 339-343, Jun. 2003.
Vaquero, et al., "A depth-encoding PET detector module with improved spatial sampling", 1998 Conf. Rec. IEEE NSS and MC Conf. M6-29.
Moses, et al., "Design Studies for a PET detector module using a PIN photodiode to measure depth of interaction", IEEE Trans. Nucl. Sci. 41, 1441-1445, 1994.
Bauer, et al., "Measurements and Ray-Tracing Simulations of Light Spread in LSO Crystals," Nuclear Science, IEEE Transactions on , vol. 56, No. 5, pp. 2566-2573, Oct. 2009.
Llosa, et al., "First Results in the application of Silicon Photomultiplier matrices to small animal PET", NDIP08 conference talk, Aix les Bains, Jun. 15-20, 2008, pp. 1-22.

\* cited by examiner

SYSTEM AND METHOD FOR PROVIDING DEPTH OF INTERACTION DETECTION USING POSITRON EMISSION TOMOGRAPHY

CROSS-REFERENCE TO RELATED APPLICATIONS AND CLAIM FOR PRIORITY

This application is a non-provisional of, and claims priority under 35 U.S.C. §119(e) from, provisional application Ser. No. 61/300,146, filed Feb. 1, 2010, entitled "PET Detector With Depth-Of-Interaction Resolution", the entire disclosure of which is incorporated herein by reference into the present application.

TECHNICAL FIELD

In general, the invention relates to nuclear medical imaging. More particularly, the invention relates to gamma radiation detectors used, for example, in positron emission tomography (PET) scanning.

BACKGROUND

In PET imaging, positrons are emitted from a radiopharmaceutically doped organ or tissue mass of interest. The positrons combine with electrons and are annihilated and, in general, two gamma photons which travel in diametrically opposite directions are generated upon that annihilation. Opposing crystal detectors, which each scintillate upon being struck by a gamma photon, are used to detect the emitted gamma photons. By identifying the location of each of two essentially simultaneous gamma interactions as evidenced by two essentially simultaneous scintillation events, a line in space along which the two gamma photons have traveled (a "line of response," or "LOR") can be determined. The LORs associated with many million gamma interactions with the detectors are calculated and "composited" to generate an image of the organ or tissue mass of interest, as is known in the art.

In some of the earlier PET systems, the gamma detectors could be used only to determine the location of gamma interaction with the detector in two dimensions, which gave rise to parallax errors. More particularly, a conventional two-dimensional measurement of the spatial location of a detected gamma ray absorption event in the scintillating crystal is limited to a two-dimensional point in the X,Y plane of the crystal. However, because the number of scintillation photons reaching each detector element (e.g., either a PMT or a photodiode) is dependent on the solid angle subtended by the area of that detector element to the point of the gamma ray absorption within the crystal, the amount of scintillation photons received by each detector is also a function of the depth of interaction (DOI) of the incident gamma ray within the crystal, i.e., along the Z axis of the crystal.

The DOI is an important parameter when applied to imaging detector geometries where the directions from which incident gamma rays impinge upon the crystal are not all substantially normal to the crystal surface. If incident gamma rays intersect the crystal from directions not normal to the crystal, the unknown depth of interaction of those gamma rays within the crystal will result in an additional uncertainty in the measured position of the interaction because of the parallax effect, if only a two dimensional (i.e., X,Y) spatial location is calculated for such an absorption event. A detailed explanation of the importance of and the problems associated with the DOI is provided in "Maximum Likelihood Positioning in the Scintillation Camera Using Depth of Interaction," D. Gagnon et al., IEEE Transactions on Medical Imaging, Vol. 12, No. 1, March 1993, pp. 101-107.

Thus, parallax errors could be reduced by using depth of interaction (DOI) information to increase the spatial resolution of the system, i.e., to provide the location of gamma interaction in three dimensions in space. In this regard, some research brain PET scanners are able to provide DOI information using so-called "phoswich" (for "phosphorescence sandwich") detectors, constructed as axially stacked scintillators, using a pulse shape discrimination method to minimize parallax error as disclosed in U.S. Pat. No. 6,288,399 to Andreaco et al.

The articles J. Vaquero et al., "A depth-encoding PET detector module with improved spatial sampling". 1998 Conf. Rec. IEEE NSS and MC Conf. M6-29 and F. Cayouette et al., "Monte Carlo simulation using Detect 2000 of a multilayered scintillation block and fit to experimental data". IEEE Trans. Nucl. Sci. 50, 339-343, 2003 describe another solution for measuring DOI. Their approach describes the use of two layers of crystal arrays that are offset in the x and y direction. This allows the identification of depth by assigning the events to one of the layers with the superimposed, overall crystal map. This concept is often used in combination with multi-anode PMTs, because a large number of channels is required to achieve the necessary position resolution US Patent Application No. 2007/0090298 by Shao and the article W. Moses and S. Derenzo, "Design studies for a PET detector module using a PIN photodiode to measure depth of interaction". IEEE Trans. Nucl. Sci. 41, 1441-1445, 1994 describe still another approach for measuring DOI. In their approach, detectors with dual-ended readout of the scintillator array are used. This is particularly advantageous in combination with thin photosensors such as PIN photodiodes, avalanche photodiodes (APDs) or silicon photomultipliers (SiPMs). Those thin photosensors can be coupled to the scintillator even on the side facing the incident radiation, without leading to high absorption losses and without using much space. DOI information is then obtained by analysing the ratio of signals read out at either end of the scintillator.

The use of multiple, stacked detector modules, each consisting of a scintillator block read out by a number of photosensors is described in G. Llosa, "Experimental results and applications of FBK-irst SiPM pixels and matrices by the DASIPM collaboration", NDIP08 Conference Talk. This is approach is used in combination with thin photosensors such as SiPMs, that do not occupy much space in between the scintillator layers.

Lewellen et al. have proposed an approach in "DMice—a depth-of-interaction detector design for PET scanners", 2004 Conf. Rec. IEEE NSS and MIC, and in U.S. Patent Application No. 2009/0224164, to obtain DOI information by measuring the degree of light sharing for pairs of crystals with a systematically varied optical coupling along the common interface. Detector blocks are then assembled from a multitude of such pairs. Their read-out relies on a one-on-one coupling scheme, where each of the crystals in a pair is co-registered with the anode pad of a multi-anode PMT or a SiPM read-out channel. The result is an encoding of the DOI information in the one-dimensional light sharing profile within each crystal pair.

However, each of these approaches have deficiencies such as high cost, difficulty of implementation, need for additional equipment, and the like.

There remains a need in the art, however, for further improvement in the light collection efficiency and spatial resolution of such a DOI scintillation detector.

SUMMARY

A system and method is provided for determining depth of interaction (DOI) information. The system and method includes a detector configured to generate DOI information as a result of radiation emitted from a radiation source. The system and method further includes a plurality of scintillator pixels forming a block, wherein the plurality of scintillator pixels have a first portion and a second portion. A first medium distributed in an alternating pattern of coupling and separation between each of the scintillator pixels in a first portion or second portion of the block is also provided. A plurality of sensors for detecting scintillation events across the plurality of scintillators based on the alternating pattern of coupling and separation between each of the scintillator pixels, wherein DOI information is provided by a position profile of the block, and an image processor for generating a 3 dimensional image from the DOI information are also included.

Additional aspects and technical effects of the present disclosure will become readily apparent to those skilled in the art from the following detailed description wherein embodiments of the present disclosure are described simply by way of illustration of the best mode contemplated to carry out the present disclosure. As will be realized, the present disclosure is capable of other and different embodiments, and its several details are capable of modifications in various obvious respects, all without departing from the present disclosure. Accordingly, the drawings and description are to be regarded as illustrative in nature, and not as restrictive.

BRIEF DESCRIPTION OF THE DRAWINGS

The present disclosure is illustrated by way of example, and not by way of limitation, in the figures of the accompanying drawing and in which like reference numerals refer to similar elements and in which.

DETAILED DESCRIPTION

In the following description, for the purposes of explanation, numerous specific details are set forth in order to provide a thorough understanding of exemplary embodiments. It should be apparent, however, that exemplary embodiments may be practiced without these specific details or with an equivalent arrangement. In other instances, well-known structures and devices are shown in block diagram form in order to avoid unnecessarily obscuring exemplary embodiments.

Figure 1:
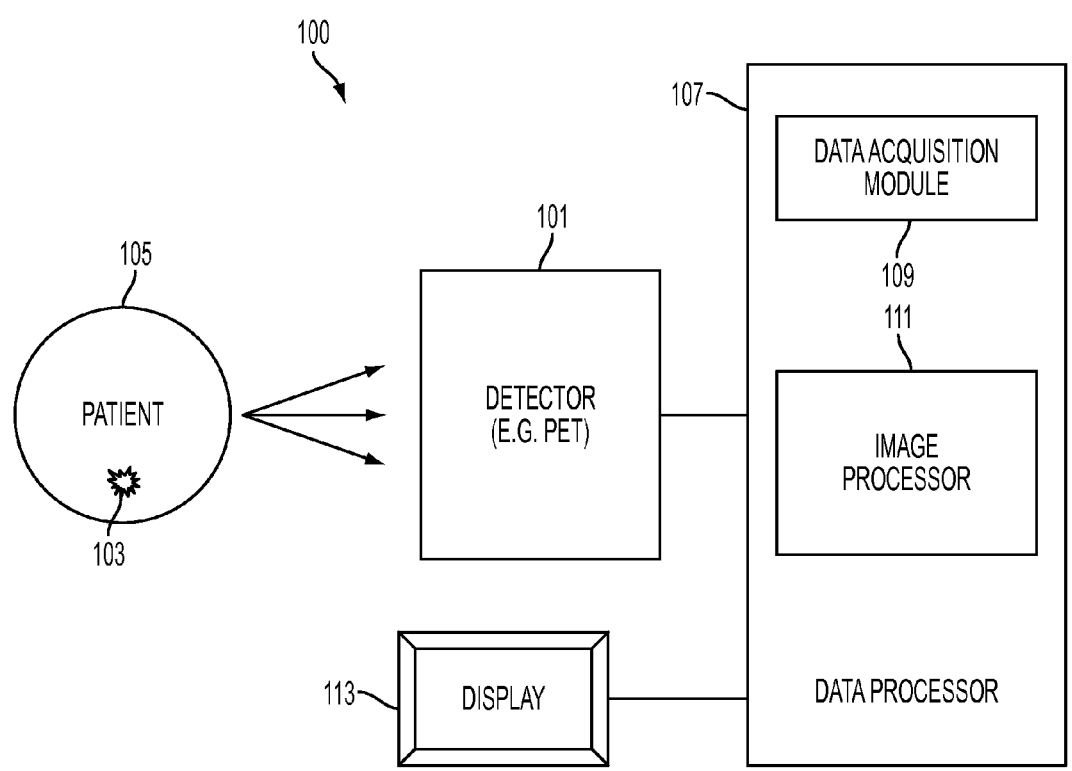
FIG. 1 is a diagram of a detection system utilizing a positron emission tomography (PET) scintillation block for generating depth-of-interaction (DOI) information, according to various embodiments.

FIG. 1 is a diagram of a detection system utilizing a PET scintillation block for generating depth-of-interaction (DOI) information, according to various embodiments. As shown, a detection system 100 includes a detector 101 to observe events stemming from a radiation source 103 emitting radiation (e.g., gamma rays) from a subject (patient) 105. The detector 101 outputs data to a data processor 107, which includes a data acquisition module 109 and an image processor 111. The data acquisition module 109 uses spatial coordinate signals to produce input to the image processor 111. The image processor 111 can then produce, for example, an image of tissues in the patient 105. The image can then be displayed on a display unit 113.

The system 100 provides a high spatial resolution PET detector with DOI capability. The DOI information is obtained from the details of the position profile. This is preferably achieved by systematically varying the optical coupling between scintillator pixels as a function of vertical position within the pixels e.g., using an alternating pattern of coupling and separating the pixel interfaces at the bottom and/or top of crystal block. The three-dimensional light sharing over the whole crystal block is influenced by the optical coupling configuration in the vicinity of the interaction site, and the DOI information becomes encoded in the position profile using various embodiments.

Figure 2A:
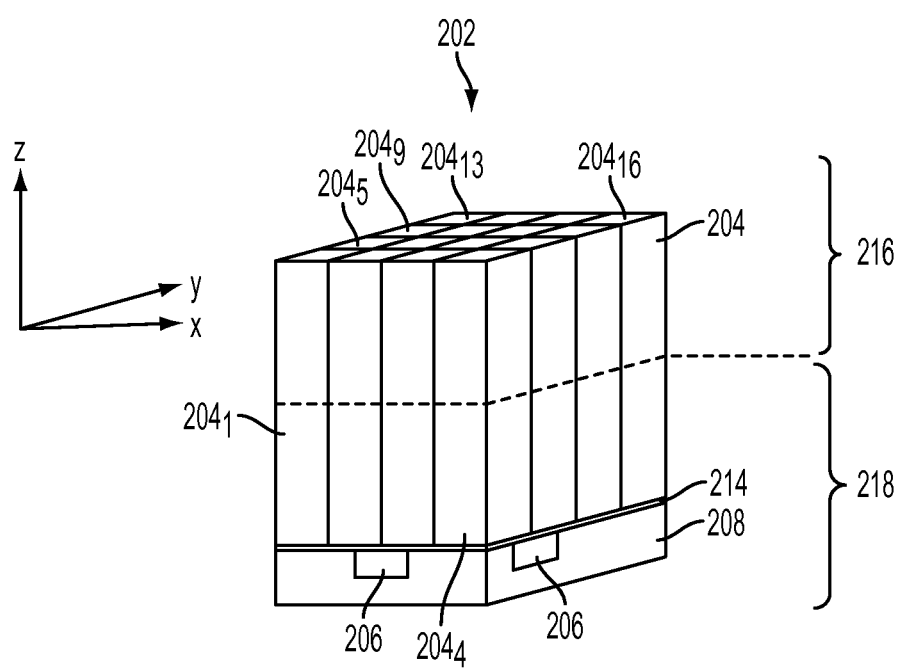
FIG. 2A is a diagram depicting a DOI PET block detector, based on an exemplary array of 4×4 scintillator crystals and 2×2 optical sensors in accordance with an embodiment of the present invention.

FIG. 2A is a diagram depicting a DOI PET block detector 101, based on an exemplary array of 4×4 scintillator pixels 204 comprising crystal pixel $204_1$ to $204_{16}$, 2×2 optical sensors 206 coupled to the scintillator pixel array 204 by sensor mount 208 via coupling film 214 in accordance with an embodiment of the present invention. The plurality of scintillator pixels is selected from the group consisting of a LSO crystal, a GSO crystal, a LuAP crystal, a LYSO crystal, a BGO crystal, LFS crystal, a NAI crystal, CSI crystal, and a LGSO crystal.

Optical sensors 206 are selected from the group consisting of a solid state detector, a photomultiplier tube, a SiPM, a pin diode, a CCD, and an avalanche photodiode.

U.S. Pat. No. 7,019,297 to Aykac which is incorporated herein by reference and is commonly assigned discloses exemplary optical coupler and separator materials that can be used. However, the invention is not limited to those materials.

Incident radiation 202 impacts the scintillator crystals 204. In accordance with various embodiments of the invention optical couplers, optical separators, air gaps, thin films and the like distributed in positions throughout the scintillator crystals 204 are used to control light distribution throughout the crystal block.

It should be appreciated by those skilled in the art that although a 4×4 scintillator pixel array is disclosed with a 2×2 optical sensor, the invention is not limited to this configuration. Other configurations of arrays and sensors can be used without departing from the scope of the present invention.

Figure 2B:
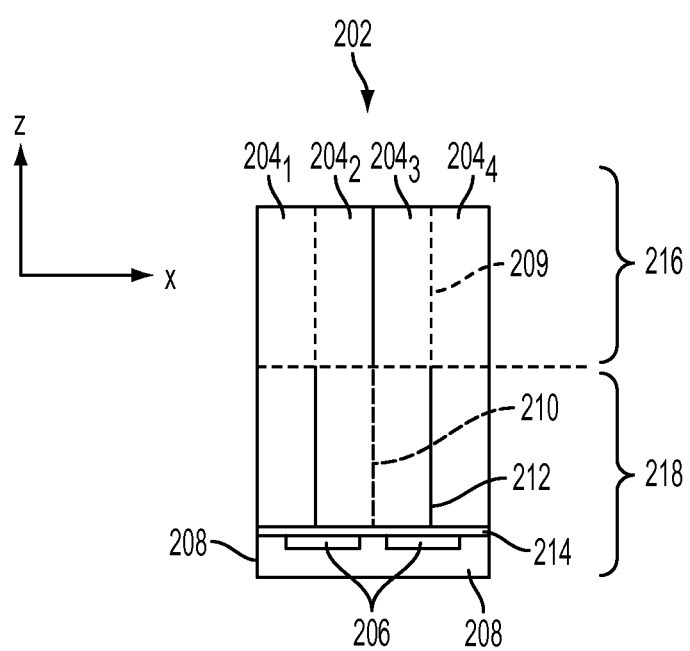
FIG. 2B is a diagram depicting a cross sectional view along the xz plane of the z-position dependent optical coupling structures between crystals in accordance with an embodiment of the present invention.
Figure 3A:
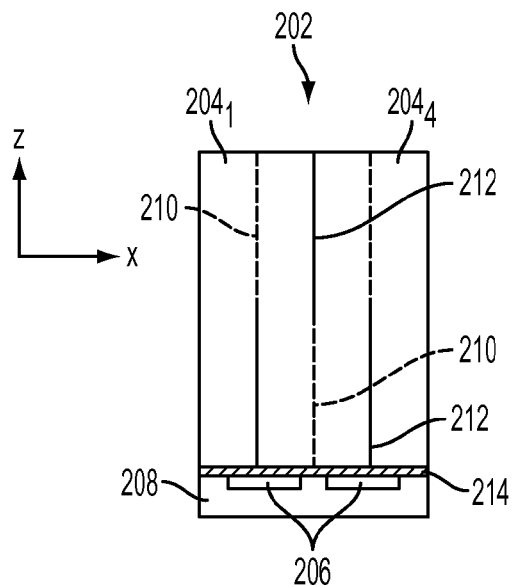
FIG. 3A is a diagram of a DOI block having couplers, separators and a light guide in accordance with an embodiment of the present invention.
Figure 3B:
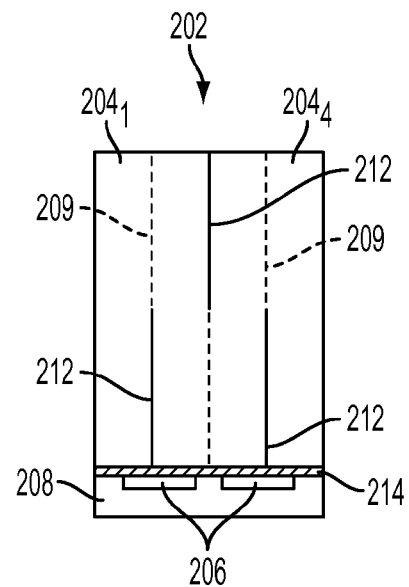
FIG. 3B is a diagram of a DOI block having separators and a light guide in accordance with an embodiment of the present invention.
Figure 3C:
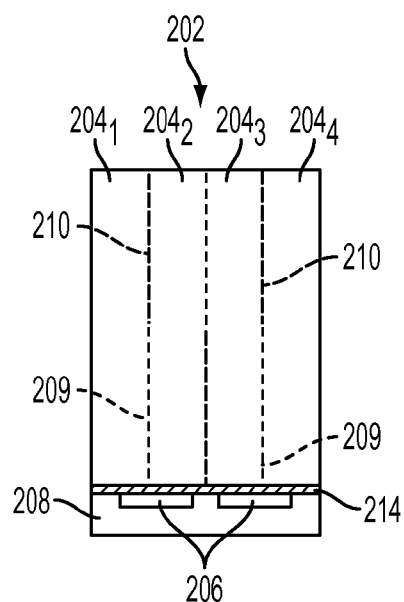
FIG. 3C is a diagram of a DOI block having couplers and a light guide in accordance with an embodiment of the present invention.
Figure 3D:
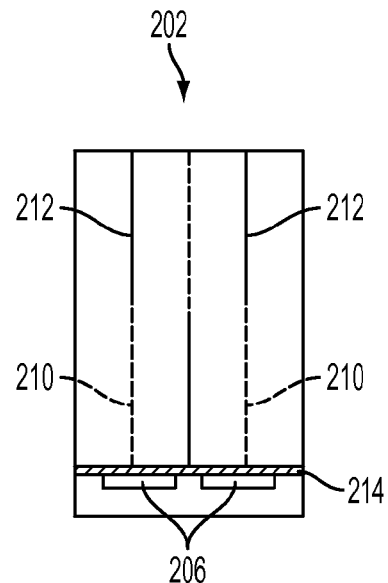
FIG. 3D is a diagram of a DOI block having couplers, separators and a light guide all in an inverted position in accordance with an embodiment of the present invention.
Figure 3E:
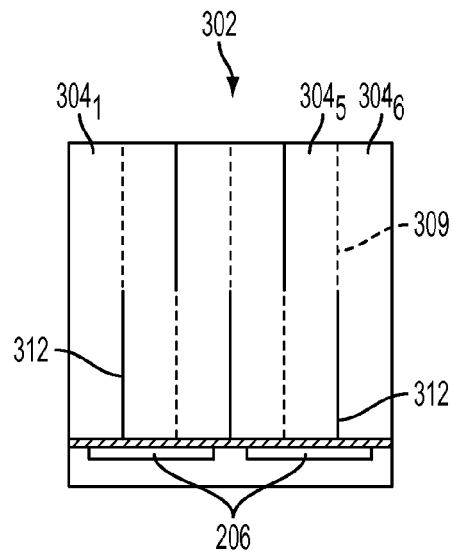
FIG. 3E is a diagram of a DOI block having 6×6 crystals coupled to 2×2 sensors, with alternating separator structures in accordance with an embodiment of the present invention.
Figure 3F:
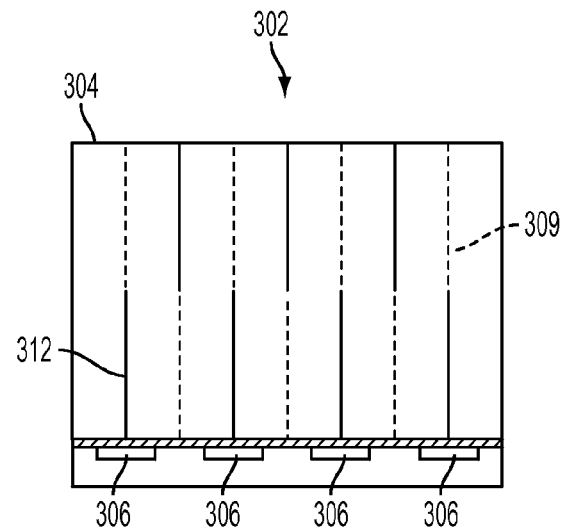
FIG. 3F is a diagram of a DOI block having 8×8 crystals coupled to 4×4 sensors, with alternating separators in accordance with an embodiment of the present invention.
Figure 3G:
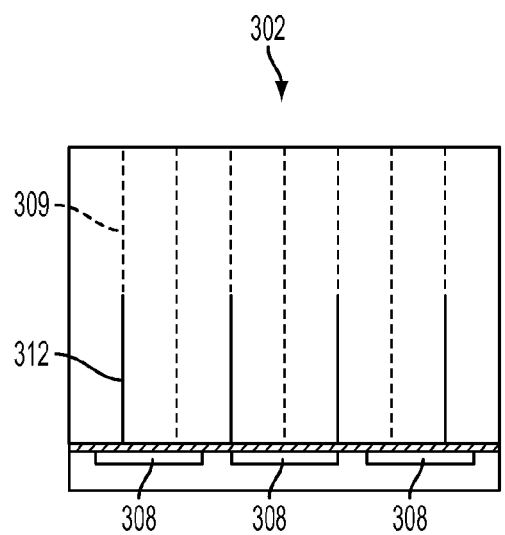
FIG. 3G is a diagram of a DOI block having 8×8 crystals coupled to 3×3 sensors, with separators located at the bottom of the block in accordance with an embodiment of the present invention.

FIG. 2B is a diagram depicting a cross sectional view along the xz plane of the z-position dependent optical coupling structures between crystals in accordance with an embodiment of the present invention. Specifically, DOI block 200 depicts incident radiation 202, scintillator pixel $204_1$, $204_2$, $204_3$ and $204_4$, sensor mount 208, optical coupler 210, air gap 209, optical separator 212 and coupling film 214. The scintillator pixels are discrete crystals, which are assembled into a two-dimensional array and coupled via air gaps, optical separator foils and optical coupling foils, as shown. It should be appreciated by those skilled in the art that the invention is not limited to foils, the couplers and separators can comprise films, powders, paints, paper, plastics, metals and combinations of the materials.

In this example, the alternating use of partial optical separators at the top or upper portion 216 of the block and bottom or lower portion 218 of the block of the crystal-crystal interfaces cause a spread of the position peaks. Near the top or upper portion 216, the positions of events within the corner $204_1$, $204_4$, $204_{13}$ and $204_{16}$ and edge pixels $204_2$, $204_3$, $204_5$, $204_8$, $204_9$, $204_{12}$, $204_{14}$, and $204_{15}$ are moved inwards, because of light sharing across the air gap 209. Near the bottom or lower portion 218 of the block, the partial separators 212 lead to a more outward position of edge pixels $204_2$, $204_3$, $204_5$, $204_8$, $204_9$, $204_{12}$, $204_{14}$, and $204_{15}$ and corner pixels $204_1$, $204_4$, $204_{13}$ and $204_{16}$ because the light sharing is reduced by the optical separator 212, and many photons will hit the sensor area directly, without being reflected and scattered across the whole block.

For the four inner pixels, the effect works in a similar, but opposite way: Near the top or upper portion 216 of the block, light sharing towards the inner pixels $204_6$, $204_7$, $204_{10}$, and $204_{11}$ of the block is hindered by the separator 212, while coupling toward the corner is possible. Near the bottom or lower portion 218 of the block, a spread toward the corner is limited by the separator 212 due to reflection, whereas in this example a spread toward the other detector half is even further enhanced by an additional optical coupling film via optical coupler 210 between the crystals. Due to these conditions, events at the lower portion 218 of the block are pulled towards the center of the position profile, while events interacting near the upper portion 216 of the block are pulled further out of the position profile.

Figure 5A:
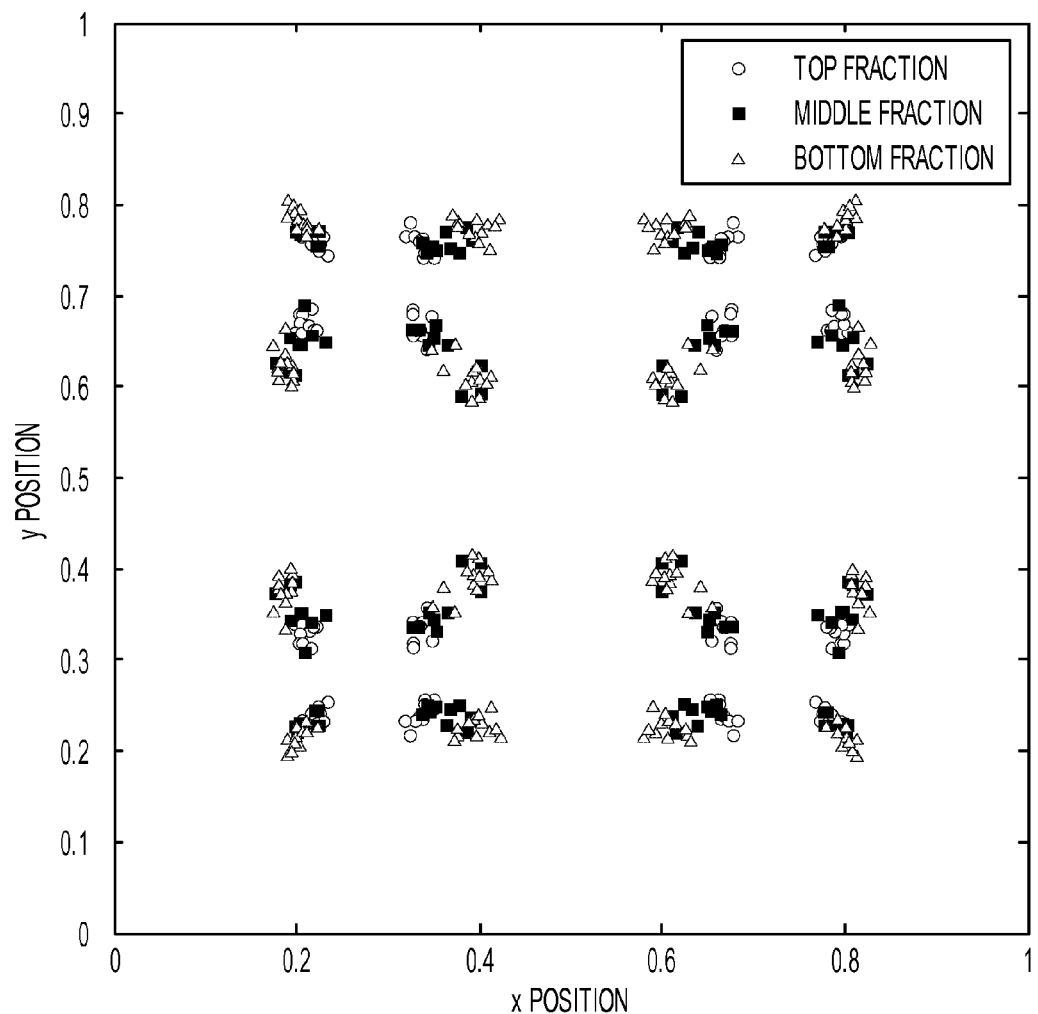
FIG. 5A is a graph depicting simulated position results for the block detector described in FIGS. 2A and 2B in accordance with an embodiment of the present invention.
Figure 5B:
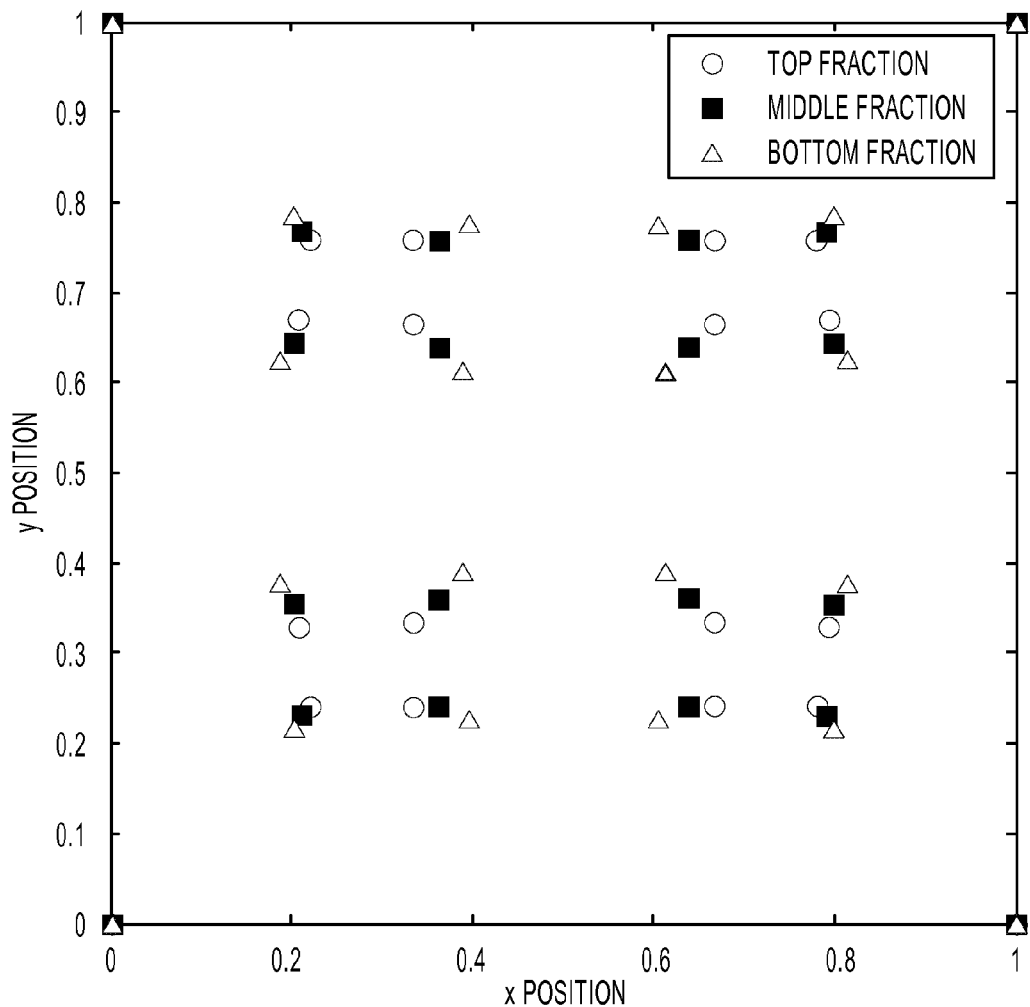
FIG. 5B is a graph depicting mean values for position results in each of three depth bins depicted in FIG. 5C in accordance with an embodiment of the present invention.
Figure 5C:
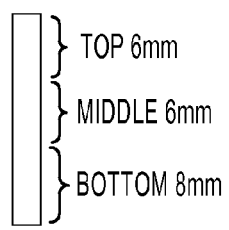
FIG. 5C is a diagram depicting three depth bins used in the graphs of FIGS. 5A and 5B in accordance with an embodiment of the present invention.

The sample block shown in FIGS. 2A, 2B, and simulated in FIGS. 5A, 5B and 5C has no additional light guide between the scintillator crystals 204 and the sensors 206 except for thin coupling film 214. In this case, the optical coupling between the crystals occurs mostly via the air gaps 209 and/or the optical coupling film used for optical coupler 210 at the central interfaces of the block. It is also possible to include additional light guiding objects to further tune the light sharing between crystals and to improve the resolution between crystals and for different interaction depths. Such additional light guides are likely to become more relevant if larger crystal arrays are used, for example, in combination with more optical sensor elements. It should be appreciated by those skilled in the art that coupling film 214 can be eliminated and a compression fit used without departing from the scope of the present invention.

The basic concept of the invention is to use partial or graded optical elements between the crystals in order to vary the light distribution over the whole block as a function of interaction height. Another embodiment to FIGS. 2A and 2B may also be achieved by the use of optical separators alone or by the use of optical couplers alone with air gaps used for the alternating pattern, for example, optical separator, then air gap and so on, or optical coupler then air gap and so on. Preferably, the arrangement is optical separator then optical coupler and so on. Similarly, it is possible to use optical coupling or separator elements only near the bottom or only near the top of the block.

A preferable arrangement for providing DOI resolution over the whole block is to use an alternating pattern of separation near the bottom/coupling near the top, then coupling near the bottom/separation near the top and so on. For a good DOI resolution of the corner pixels, it seems advantageous to start the series with separation near the bottom for the first interface from the block edge. But an inverted structure starting with separation near the top at the first interface is also possible in principle. A range of different DOI block detector examples is shown in FIG. 3.

FIG. 3 comprises various diagrams illustrating different examples of DOI resolving block detectors with different partial light sharing elements and different crystal and sensor numbers. For example, FIG. 3A is a diagram of a DOI block having couplers 210, separators 212 and a light guide 214; FIG. 3B is a diagram of a DOI block having separators 212 and a light guide 214; FIG. 3C is a diagram of a DOI block having couplers 210 and a light guide 214; FIG. 3D is a diagram of a DOI block having couplers 210, separators 212 and a light guide 214 all in an inverted position; FIG. 3E is a diagram of a DOI block having 6×6 crystals coupled to 2×2 sensors, with alternating separator structures. For example upper portion begins with an air gap 309 then separator 312 and so on in an alternating fashion. The lower portion of the block begins with separator 312 then air gap 309 then so on in an alternating fashion. FIG. 3F is a diagram of a DOI block having 8×8 crystals coupled to 4×4 sensors, with alternating separators. For example the arrangement is similar to FIG. 3E except there are more pixels and sensors. FIG. 3G is a diagram of a DOI block having 8×8 crystals coupled to 3×3 sensors, with separators 312 located only at the bottom of the block in alternating fashion with air gap 309. The upper portion of the block uses only air gaps between the pixels in accordance with an embodiment of the present invention. There are no separators 312 used in the upper portion of the block.

Other embodiments of the invention can use more than one optical separator and/or more than one optical coupling material in order to provide even more different degrees of light sharing for different depth zones. For example, different types of coupling or separation materials can be used to add greater control to scintillations across the block.

Figure 4:
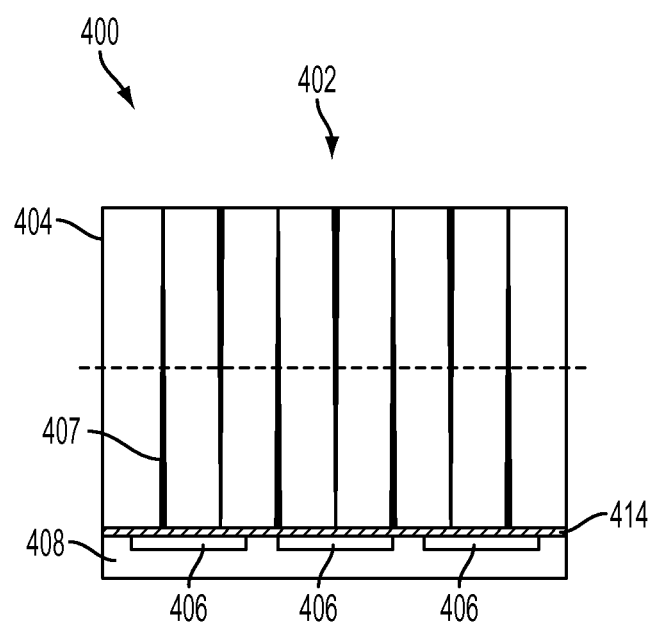
FIG. 4 is a diagram illustrating a DOI resolving PET block detector, manufactured by laser structuring of a monolithic scintillator crystal in accordance with an embodiment of the present invention; The thickness of the structures between the pixels indicates the degree of optical separation (thicker line means higher scatter probability).

FIG. 4 is a diagram illustrating a DOI block detector 400, manufactured by laser structuring of a monolithic scintillator crystal in accordance with an embodiment of the present invention. The thickness of the structures 407 between the pixels 404 indicates the degree of optical separation e.g., thicker line indicates higher scatter probability. Specifically, the DOI block detector is based on a monolithic scintillator crystal with optical structures 407 introduced afterwards. Such scintillator patterning may be achieved, for example, by laser structuring or by partial cutting of grooves between the pixels and possibly filling the grooves with optical separators, optical coupling media or coatings.

The method of optical patterning by laser structuring eliminates the need for elaborate mechanical processes and also the need for additional optical materials. Another advantage of this method is that it provides a straightforward way for a continuous change in optical separation between pixels as a function of height. This is possible because a different size and/or different density of scatter centers can be created, for example, by varying the laser power along the z direction. For a general description of the laser structuring method for PET detectors see patent application US2004/0262526A1, which is incorporated herein by reference.

It should be noted that the same effect of a graded, continuously varying scatter probability may also be achieved by a graded reflective coating, e.g. a modified version of the VM2000 reflective film by 3M, where the reflectivity varies with the z position. In this case, the structures 407 are graded wherein one end of the separator is thicker than the opposing end and represents varying reflectivity wherein a thicker line indicates higher reflectivity of such a graded reflective film, assembled between discrete scintillator pixels 404. Thus, structure 407 can comprise a graded orifice and can be considered an optical separator on one portion of the block and considered an optical coupler for an opposing vertical portion of the block. The adjacent orifice can be flipped to create an alternating couple/separator pattern.

The depth-encoding ability of aspects of the invention was verified by the use of optical simulations with the ray-tracing software ZEMAX. LSO was used as the scintillator material, with the optical parameters disclosed in U.S. Published Application No. 2009/0224164 to Lewellen et al., the contents of which are incorporated by reference.

VM2000 film by 3M was used as reflective material between the pixels (where indicated) and as a reflective wrapping around the whole block. As an optical coupling film the same acrylic carrier material was defined within the crystal gap, but without the reflective coating. The simulated crystal size was 2.5×2.5×20 mm$^3$, and four optical sensors with 3×3 mm$^2$ active area and 50% quantum efficiency were defined for light detection. The position coordinates x and y were determined from the signals on the four light sensors a, b, c, d by the equations:

$$x=(b+d)/(a+b+c+d); y=(a+b)/(a+b+c+d).$$

Simulated position results for 30 random events in each crystal are shown in FIG. 5. FIG. 5A is a graph depicting simulated position results for the block detector described in FIGS. 2A and 2B in accordance with an embodiment of the present invention; FIG. 5B is a graph depicting mean values for position results in each of three depth bins depicted in FIG. 5C in accordance with an embodiment of the present invention; and FIG. 5C is a diagram depicting three depth bins used in the graphs of FIGS. 5A and 5B in accordance with an embodiment of the present invention. The shapes of the data points indicate whether the interaction occurred in the top 6 mm of the crystal (circle), the next 6 mm near the middle (square) or the bottom 8 mm (triangle).

As seen in FIGS. 5A and 5B, the position peaks are spread out by the combined effects of the partial reflectors and partial optical couplers. As the shapes show, this spread is characteristic for the depth of interaction. All 16 pixels show a depth-dependent elongation, with the strongest (diagonal) spread observed for the four pixels near the center of the block e.g. scintillator pixel $204_6$, $204_7$, $204_{10}$, $204_{11}$. But even for the corner pixels, there is a reasonable resolution between top and bottom events. Utilizing these details of the position profile in the reconstruction leads to an improved overall spatial resolution by the reduction of parallax errors. The DOI resolution can be further improved with better photon statistics, e.g. due to a higher light output, higher quantum efficiency or higher sensor area fill factor than in this example.

FIG. 5C depicts three depths but the invention will work using two depths. Three depths were used for illustrative purposes. Upper portion 216 and lower portion 218 were illustrated as being substantially equal in size. This is preferable. However, the ratio can be 70/30 in either direction and not depart from the scope of the present invention. The vertical height of the separators are substantially the same with each other within the block. The vertical height of the optical couplers are also substantially the same with each other within the block.

Figure 6:
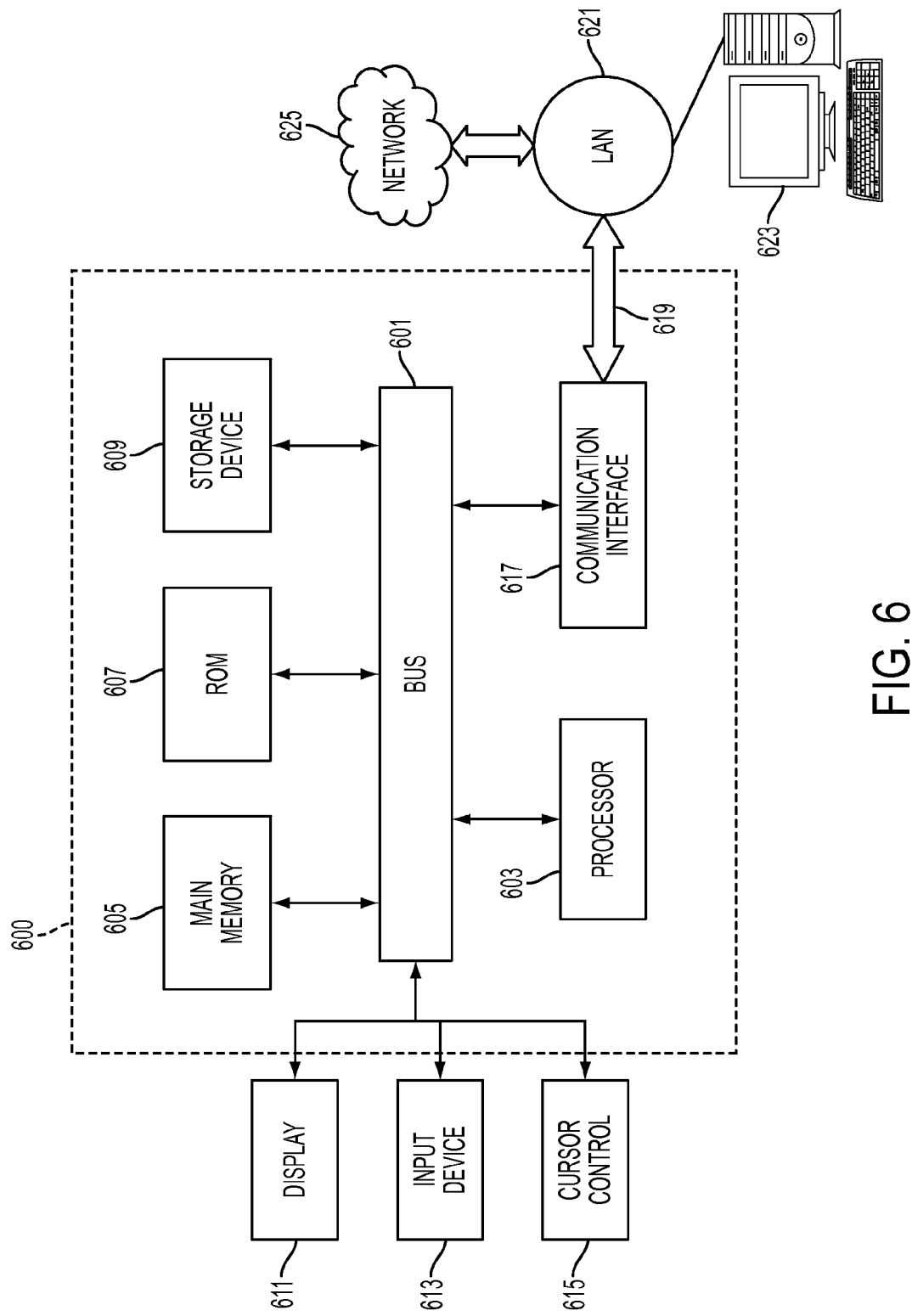
FIG. 6 is a diagram of a computing hardware that can be used to implement various embodiments of the invention.

FIG. 6 illustrates a computing hardware 600 upon which an embodiment according to various exemplary embodiments can be implemented. For example, the processes described herein can be implemented using the computer system 600. The computer system 600 includes a bus 601 or other communication mechanism for communicating information and a processor 603 coupled to the bus 601 for processing information. The computer system 600 also includes main memory 605, such as a random access memory (RAM) or other dynamic storage device, coupled to the bus 601 for storing information and instructions to be executed by the processor 603. Main memory 605 can also be used for storing temporary variables or other intermediate information during execution of instructions by the processor 603. The computer system 600 may further include a read only memory (ROM) 607 or other static storage device coupled to the bus 601 for storing static information and instructions for the processor 603. A storage device 609, such as a magnetic disk or optical disk, is coupled to the bus 601 for persistently storing information and instructions.

The computer system 600 may be coupled via the bus 601 to a display 611, such as a cathode ray tube (CRT), liquid crystal display, active matrix display, or plasma display, for displaying information to a computer user. An input device 613, such as a keyboard including alphanumeric and other keys, is coupled to the bus 601 for communicating information and command selections to the processor 603. Another type of user input device is a cursor control 615, such as a mouse, a trackball, or cursor direction keys, for communicating direction information and command selections to the processor 603 and for controlling cursor movement on the display 611.

According to one embodiment contemplated herein, the processes described are performed by the computer system 600, in response to the processor 603 executing an arrangement of instructions contained in main memory 605. Such instructions can be read into main memory 605 from another computer-readable medium, such as the storage device 609. Execution of the arrangement of instructions contained in main memory 605 causes the processor 603 to perform the process steps described herein. One or more processors in a multi-processing arrangement may also be employed to execute the instructions contained in main memory 605. In alternative embodiments, hard-wired circuitry may be used in place of or in combination with software instructions to implement the certain embodiments. Thus, the exemplary embodiments are not limited to any specific combination of hardware circuitry and software.

The computer system 600 also includes a communication interface 617 coupled to bus 601. The communication interface 617 provides a two-way data communication coupling to a network link 619 connected to a local network 621. For example, the communication interface 617 may be a digital subscriber line (DSL) card or modem, an integrated services digital network (ISDN) card, a cable modem, a telephone modem, or any other communication interface to provide a data communication connection to a corresponding type of communication line. As another example, communication interface 617 may be a local area network (LAN) card (e.g. for Ethernet, SONET or an Asynchronous Transfer Model (ATM) network) to provide a data communication connection to a compatible LAN. Wireless links can also be implemented. In any such implementation, communication interface 617 sends and receives electrical, electromagnetic, or optical signals that carry digital data streams representing various types of information. Further, the communication interface 617 can include peripheral interface devices, such as a Universal Serial Bus (USB) interface, a PCMCIA (Personal Computer Memory Card International Association) interface, etc. Although a single communication interface 617 is depicted in FIG. 6, multiple communication interfaces can also be employed.

The network link 619 typically provides data communication through one or more networks to other data devices. For example, the network link 619 may provide a connection through local network 621 to a host computer 623, which has connectivity to a network 625 (e.g. a wide area network (WAN) or the global packet data communication network now commonly referred to as the "Internet") or to data equipment operated by a service provider. The local network 621 and the network 625 both use electrical, electromagnetic, or optical signals to convey information and instructions. The signals through the various networks and the signals on the network link 619 and through the communication interface 617, which communicate digital data with the computer system 600, are exemplary forms of carrier waves bearing the information and instructions.

The computer system 600 can send messages and receive data, including program code, through the network(s), the network link 619, and the communication interface 617. In the Internet example, a server (not shown) might transmit requested code belonging to an application program for implementing an exemplary embodiment through the network 625, the local network 621 and the communication interface 617. The processor 603 may execute the transmitted code while being received and/or store the code in the storage device 609, or other non-volatile storage for later execution. In this manner, the computer system 600 may obtain application code in the form of a carrier wave.

The term "computer-readable medium" as used herein refers to any medium that participates in providing instructions to the processor 603 for execution. Such a medium may take many forms, including but not limited to non-volatile media, volatile media, and transmission media. Non-volatile media include, for example, optical or magnetic disks, such as the storage device 609. Volatile media include dynamic memory, such as main memory 605. Transmission media include coaxial cables, copper wire and fiber optics, including the wires that comprise the bus 601. Transmission media can also take the form of acoustic, optical, or electromagnetic waves, such as those generated during radio frequency (RF) and infrared (IR) data communications. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, and EPROM, a FLASH-EPROM, any other memory chip or cartridge, a carrier wave, or any other medium from which a computer can read.

Various forms of computer-readable media may be involved in providing instructions to a processor for execution. For example, the instructions for carrying out various exemplary embodiments may initially be borne on a magnetic disk of a remote computer. In such a scenario, the remote computer loads the instructions into main memory and sends the instructions over a telephone line using a modem. A modem of a local computer system receives the data on the telephone line and uses an infrared transmitter to convert the data to an infrared signal and transmit the infrared signal to a portable computing device, such as a personal digital assistant (PDA) or a laptop. An infrared detector on the portable computing device receives the information and instructions borne by the infrared signal and places the data on a bus. The bus conveys the data to main memory, from which a processor retrieves and executes the instructions. The instructions received by main memory can optionally be stored on storage device either before or after execution by processor.

The data and imaging processes described herein may be implemented via software, hardware (e.g., general processor, Digital Signal Processing (DSP) chip, an Application Specific Integrated Circuit (ASIC), Field Programmable Gate Arrays (FPGAs), etc.), firmware or a combination thereof. Such exemplary hardware for performing the described functions is detailed below.

The embodiments of the present invention can achieve several technical effects, including not requiring differential pulse shape discrimination, not requiring the use of materials with different emission decay times. Therefore the fastest and best scintillator material can be used for the whole block. This advantage is particularly relevant for making a DOI resolving time-of-flight PET detectors. The number of scintillator pixels is not higher than what is necessary for the required spatial resolution. For example, the number of scintillation pixels is not increased to provide DOI information. The blocks are relatively easy to manufacture, since there are no additional requirements for the scintillator material, in particular no additional layering of the scintillator itself along the z direction. Optical multiplexing can be used, for example, the number of read-out channels can be lower than the crystal number. Embodiments of the present invention are not restricted to the use of any particular sensor type. The embodiments work with PMTs as well as silicon based photosensors such as APDs and SiPMs.

In terms of medical imaging an advantage for PET imaging is that the DOI information will help to provide better spatial resolution in the reconstructed images, especially for off-center positions. The use of DOI information can also help to reduce the PET ring diameters to the size needed to accommodate patients and therefore reduce overall system cost.

The present disclosure enjoys industrial applicability in medical imaging, but other applications and uses can be found such as oil exploration, optical data storage, lasers, and homeland security.

In the preceding description, the present disclosure is described with reference to specifically exemplary embodiments thereof. It will, however, be evident that various modifications and changes may be made thereto without departing from the broader spirit and scope of the present disclosure, as set forth in the claims. The specification and drawings are, accordingly, to be regarded as illustrative and not as restrictive. It is understood that the present disclosure is capable of using various other combinations and embodiments and is capable of any changes or modifications within the scope of the inventive concept as expressed herein.

What is claimed is:

1. A system comprising:
   a detector configured to generate depth of interaction (DOI) information of radiation emitted from a radiation source, the detector including:
   a plurality of scintillator pixels forming a block, the block having a first portion proximate a radiation incident side thereof, and a second portion proximate a sensor side thereof;
   the scintillator pixels having a pattern of optical separation media and optical coupling media disposed therebetween in said first portion, and a pattern of optical coupling media and optical separation media disposed therebetween in said second portion that is opposite to the pattern in said first portion, thereby forming a position profile of said block; and
   a plurality of sensors for detecting scintillation events in each scintillator pixel as a result of absorption of a radiation photon therein, wherein DOI information of radiation photons in each scintillator pixel is provided by detected position of the scintillation events with respect to the position profile of the block, and
   an image processor using the DOI information to reconstruct a radiation image.

2. The system of claim 1, wherein the optical coupling media comprises an optical coupling film.

3. The system of claim 1, wherein the optical separation media comprises a reflector.

4. The system of claim 1, wherein the plurality of scintillator pixels is selected from the group consisting of a LSO crystal, a GSO crystal, a LuAP crystal, a LYSO crystal, a BGO crystal, LFS crystal, a NAI crystal, CSI crystal, and a LGSO crystal.

5. The system of claim 1, wherein the sensors are selected from the group consisting of a solid state detector, a photomultiplier tube, a SiPM, a pin diode, a CCD, and an avalanche photodiode.

6. The system of claim 1, wherein the optical coupling media comprises an air gap.

7. The system of claim 1, wherein the plurality of scintillator pixels is larger in number than the plurality of sensors.

8. The system of claim 1, wherein the first portion comprises a first half of the block and the second portion comprises a second half of the block.

9. A system comprising:
   a detector configured to generate depth of interaction (DOI) information of radiation emitted from a radiation source, the detector including:
   a monolithic scintillator block having a plurality of laser-formed scintillator pixels therein, the block having a first portion proximate a radiation incident side thereof, and a second portion proximate a sensor side thereof, the scintillator pixels having a first pattern of laser-formed optical separation structures disposed therebetween in said first portion, and a pattern of laser-formed optical separation structures disposed therebetween in said second portion that is opposite to said first pattern, thereby forming a position profile of said block; and
   at least one sensor for detecting scintillation events in each scintillator pixel as a result of absorption of a radiation photon therein, wherein DOI information of radiation photons in each scintillator pixel is provided by detected position of the scintillation events with respect to the position profile of the block, and
   an image processor using the DOI information to reconstruct a radiation image.

10. The system of claim 9, wherein optical separation between pixels is a function of laser pattern height.

11. The system of claim 9, wherein the first portion comprises a first half of the block and the second portion comprises a second half of the block.

12. The system of claim 9, wherein the laser patterns of the scintillator comprises voids or cuts.

13. The system of claim 12, wherein the voids or cuts are filled with at least one of an optical coupling medium and optical separating medium.

14. The system of claim 9, wherein the scintillator block is selected from the group consisting of a LSO crystal, a GSO crystal, a LuAP crystal, a LYSO crystal, a BGO crystal, LFS crystal, a NAI crystal, CSI crystal, and a LGSO crystal.

15. A method of providing depth of interaction (DOI) information of radiation emitted from a radiation source, comprising:
   defining separate portions of a scintillator pixel array as a first portion proximate a radiation incident side thereof and a second portion proximate a scintillation detector side thereof;
   forming a first pattern of optical coupling and optical separation between pixels in said first portion;
   forming a second pattern of optical separation and optical coupling between pixels in said second portion that is opposite to said first pattern;
   said first and second patterns defining a position profile of said scintillator pixel array providing a plurality of scintillator pixels forming a block, wherein detection of scintillation event position distributions in said scintillator pixel array provides DOI information in accordance with the position profile.

* * * * *